United States Patent [19]

Hall

[11] 4,427,381
[45] Jan. 24, 1984

[54] COMBINATION LIGHT WIRE AND EDGEWISE APPLIANCE

[75] Inventor: Arthur B. Hall, LaPorte, Ind.

[73] Assignee: TP Laboratories, Inc., Westville, Ind.

[21] Appl. No.: 443,458

[22] Filed: Nov. 22, 1982

[51] Int. Cl.³ .............................................. A61C 7/00
[52] U.S. Cl. ..................................................... 433/14
[58] Field of Search ........................... 433/14, 16, 8, 9

[56] References Cited

U.S. PATENT DOCUMENTS 2,196,516  4/1940  Atkinson .................................. 433/8
4,212,638  7/1980  Korn ....................................... 433/8

*Primary Examiner*—Robert Peshock
*Attorney, Agent, or Firm*—Lloyd L. Zickert

[57] ABSTRACT

A combination light wire and edgewise appliance for selectively treating a patient by the light wire technique or the edgewise technique, which includes a light wire bracket having a mesiodistally extending archwire slot and an occlusogingivally extending lock pin opening to which may be secured a round archwire by a lock pin and an edgewise module mountable on and securable to the bracket and having a mesiodistally extending and labiobuccally opening rectangular archwire slot, and ligating wings to which may be mounted a rectangular archwire and secured thereto by suitable ligatures.

28 Claims, 31 Drawing Figures

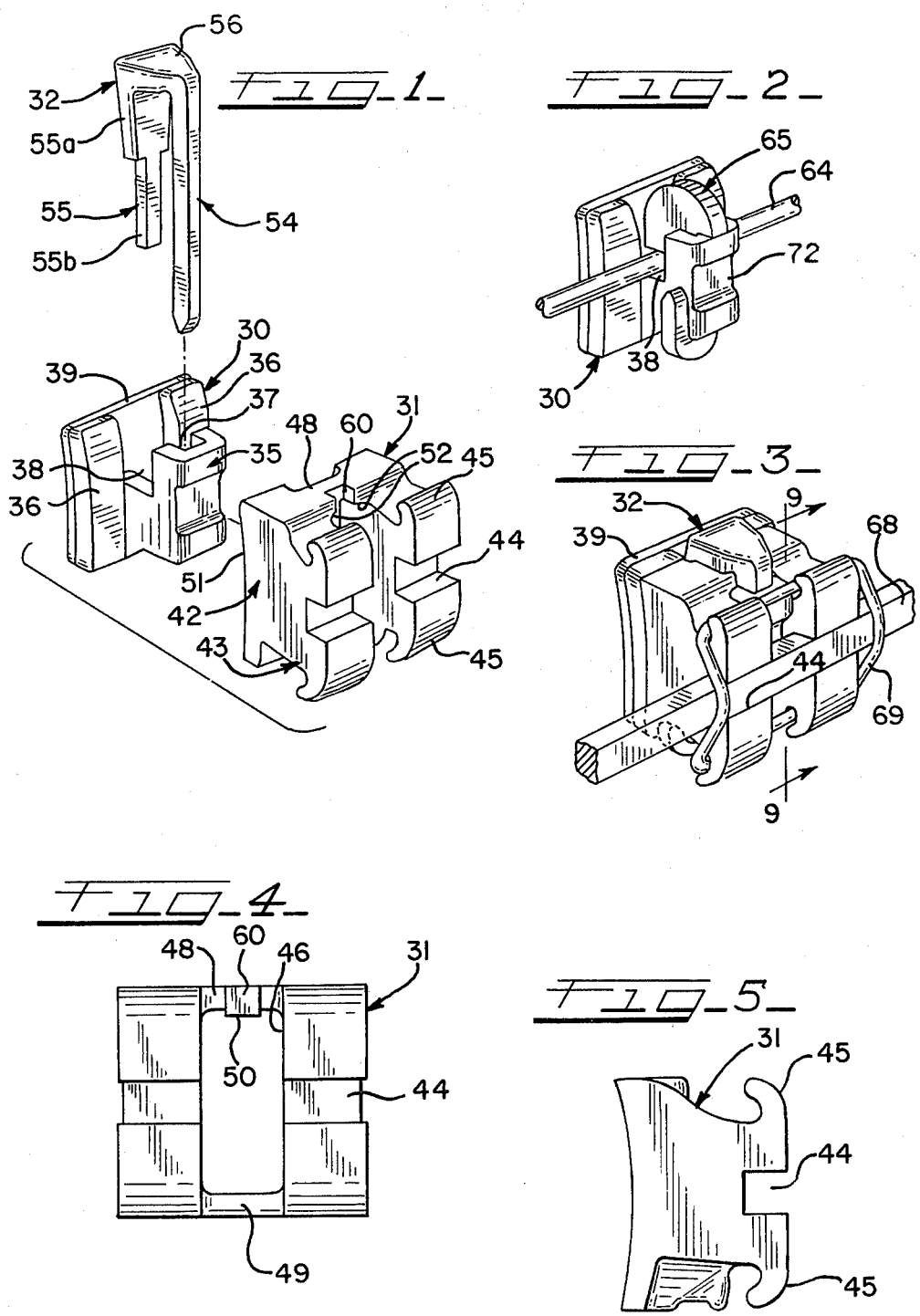

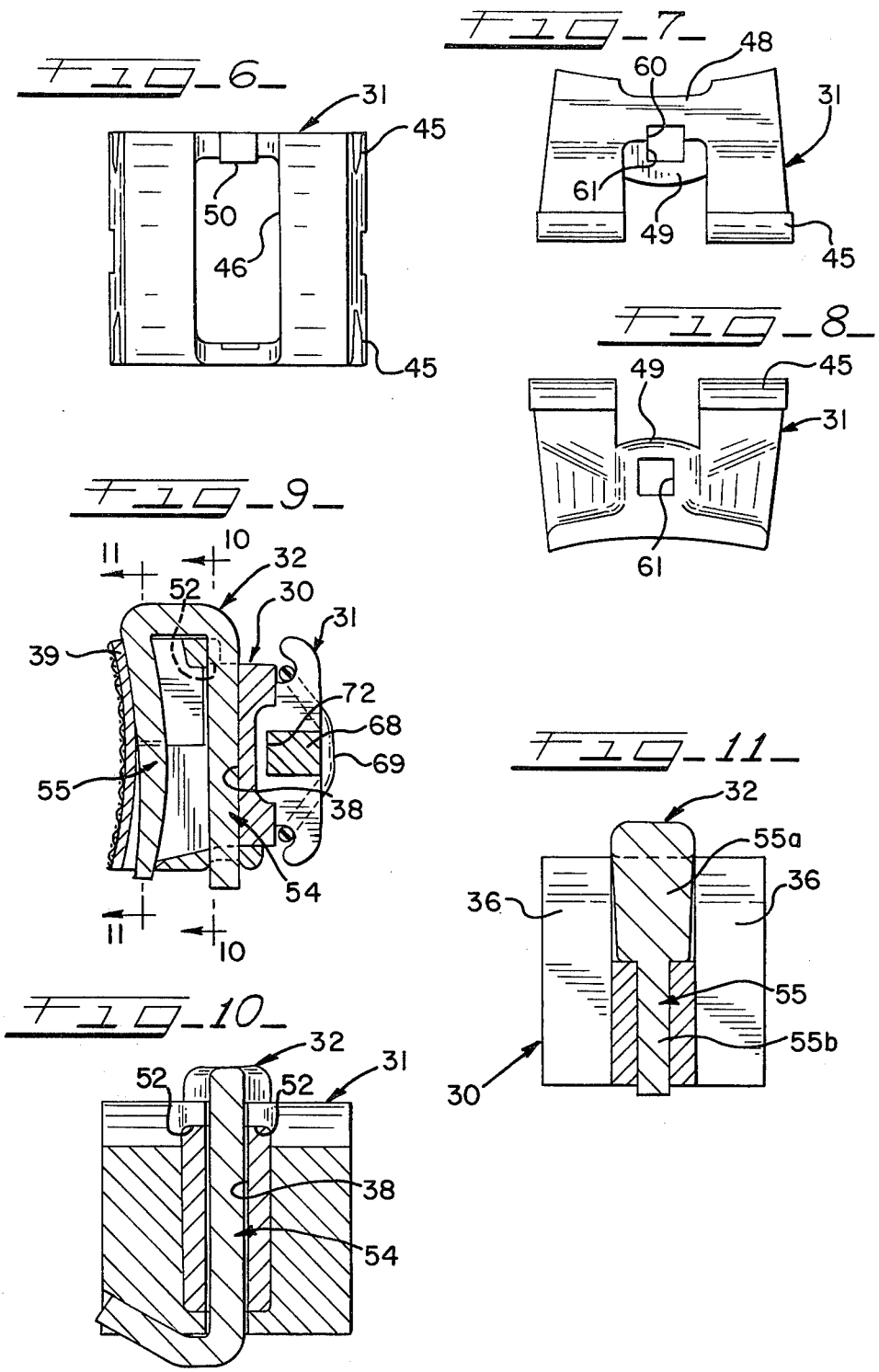

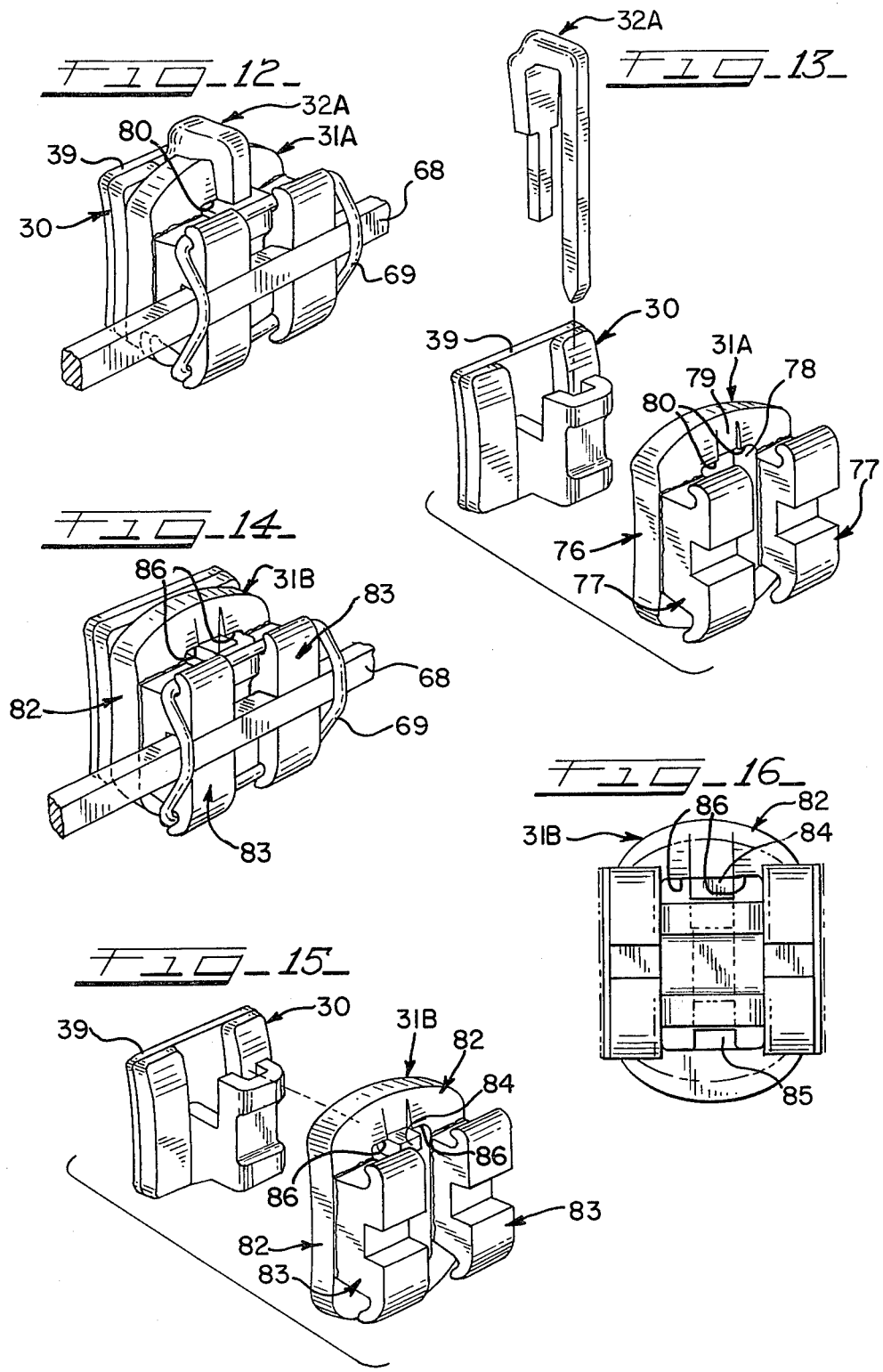

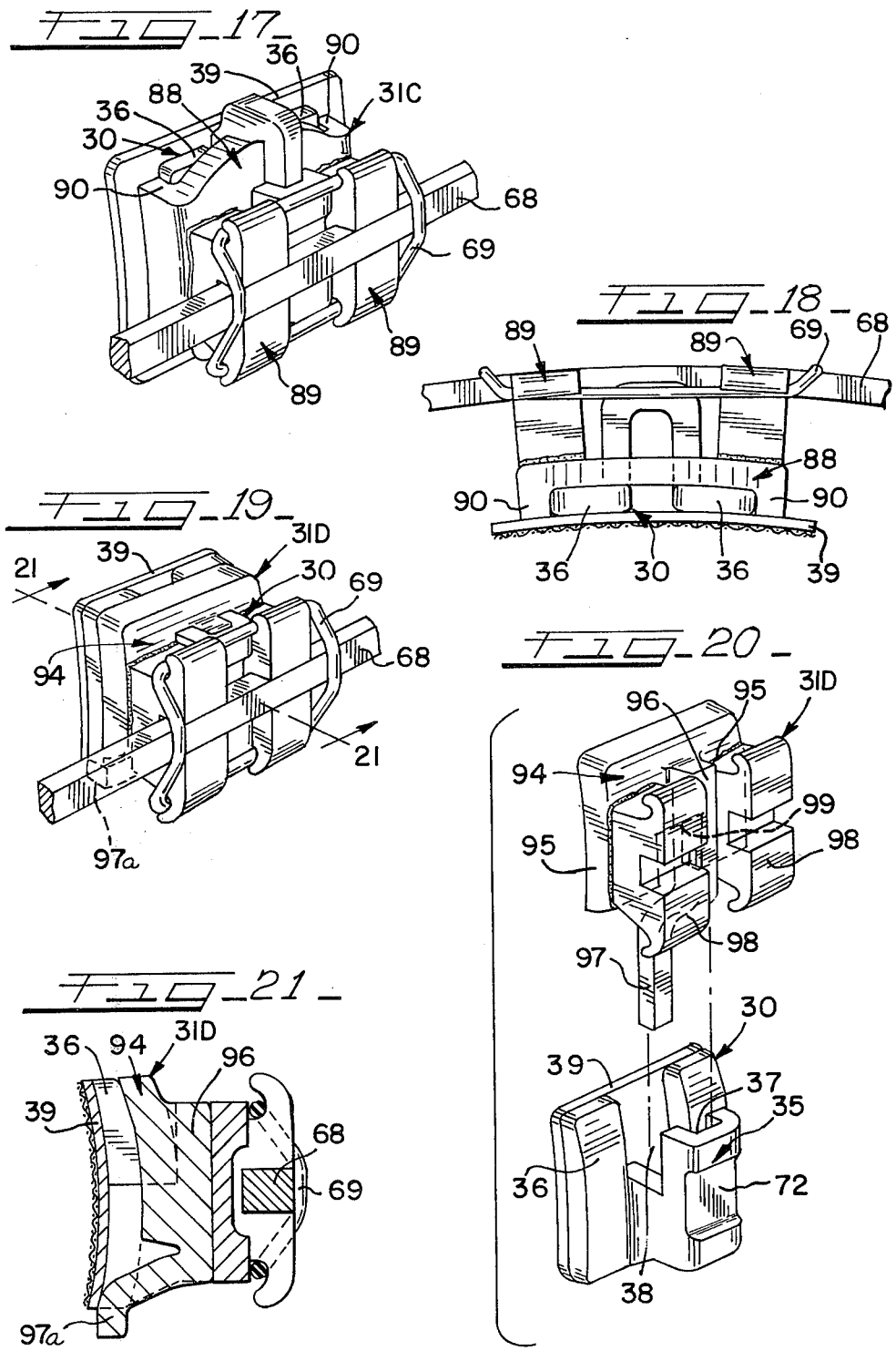

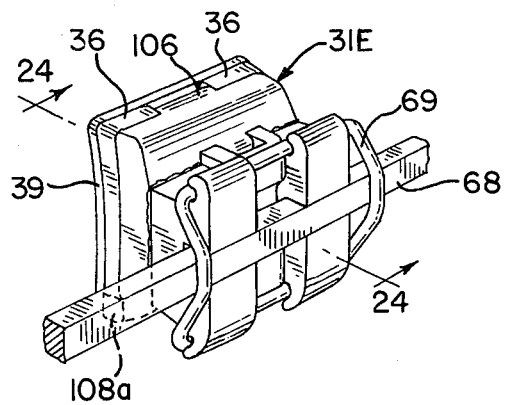
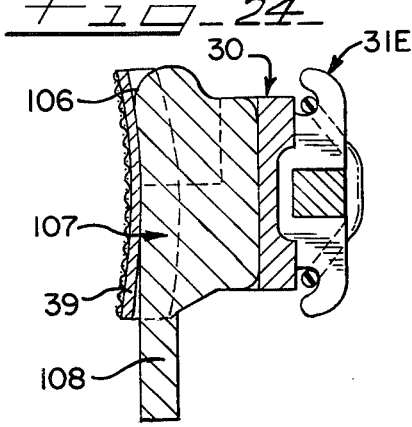
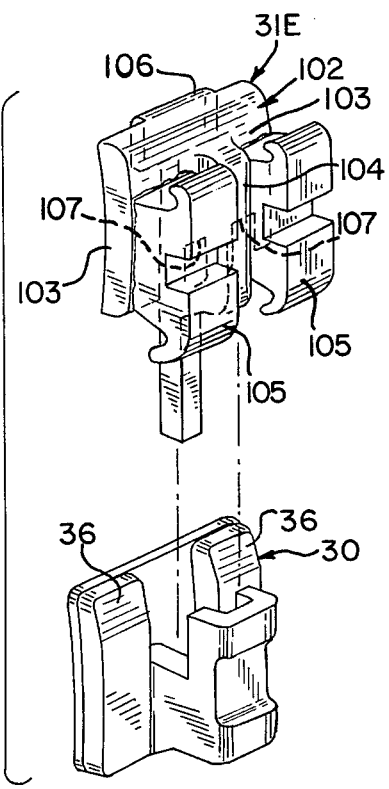
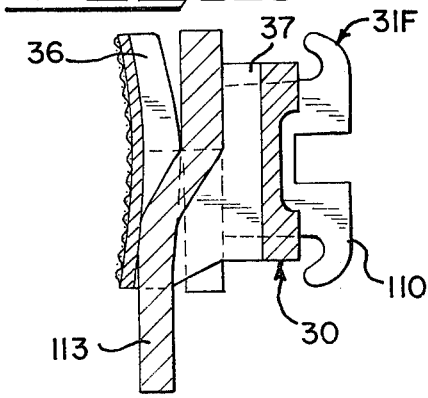
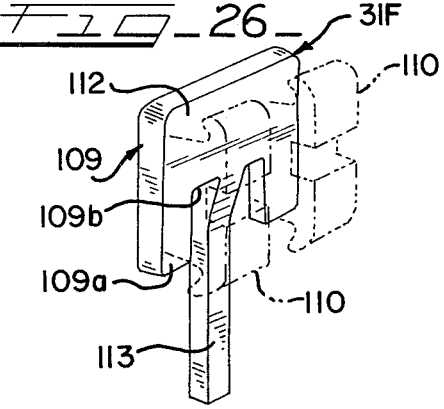

COMBINATION LIGHT WIRE AND EDGEWISE APPLIANCE

This invention relates in general to an orthodontic appliance, and more particularly to an orthodontic appliance that is capable of being selectively used for the treatment of patients either by the light wire technique or the edgewise technique, and more particularly to a combination light wire and edgewise appliance that may be quickly and easily converted for use in a light wire system or an edgewise system without requiring the remounting on a tooth.

BACKGROUND OF THE INVENTION

The orthodontic treatment of a patient concerns the movement of teeth through the application of forces to bring them into ideal arch and occlusion position. Forces are applied to the teeth by mounting brackets on the teeth and interconnecting the brackets with archwire which is activated to apply forces to effect teeth movement. While other auxiliaries are also used to effect teeth movement, primary forces are generated by one or more archwires which are made of a spring-like metal. Thus, connecting the archwire to teeth requires the mounting of brackets to the teeth which include archwire slots for receiving the archwire. Brackets are mounted on teeth by either attaching the brackets to bands that are in turn cemented to teeth or attaching the brackets to direct bonding bases which are then direct bonded by a suitable adhesive to the teeth.

There are two primary methods or techniques utilized to orthodontically treat patients. They are the light wire technique or system and the edgewise technique or system. The light wire technique basically uses light wire brackets and round archwire and depends upon the generation of light forces to effect teeth movement. The round archwire is usually secured to the brackets by lock pins that allow free tipping between the archwire and the teeth. Edgewise brackets and rectangular archwire provide the basic items used for the edgewise system. The rectangular wire is matingly received in rectangular archwire slots of the brackets to define a rigid connection. Suitable elastic or wire ligatures are applied over the archwire and their brackets for securing the archwire to the brackets. This technique is dependent upon much heavier forces to effect teeth movement.

Each of the techniques has its advantages and disadvantages. For example, in the light wire technique the interconnection between the archwire and the bracket can be made to permit the tooth freedom of rotation and tipping. The interaction between an edgewise archwire and an edgewise bracket is a more rigid system which allows for more precise control of tooth movement to the final position.

During the treatment of a patient, the advantages of both systems can be utilized to effect the most efficient overall treatment of any one patient. However, it is not practical to remove brackets for use in one system and thereafter apply brackets for use in another system because of the expense and time restraints.

Heretofore, various appliances have been designed for use in both methods of treatment. For example, combination brackets having the capability of receiving light wire or edgewise wire by virtue of having two different archwire slots for these wires have been well known, as shown in U.S. Pat. Nos. 3,163,933 and 3,178,822. These appliances have not been completely satisfactory because there is a need for more flexibility in usage than is possible with them. Moreover, they are bulky and cannot place the archwires at the same level, thereby requiring the mounting of the bracket at an offset position on the tooth, making it more difficult to apply forces.

It has also been known to provide an edgewise wire appliance where the appliance includes a two-piece unit with one piece being attached to a tooth and the other piece being detachably mounted on the first piece, wherein the detachable member includes an archwire receiving slot that may be designed to provide different degrees of angulation and torque in the receiving slot. Detachable members designed to accomplish various functions can then be interchangeably mounted on the fixed piece that is mounted on the tooth. Such an appliance is shown in U.S. Pat. No. 2,908,974. However, this appliance does not have the capability of being used for the light wire technique.

Another attempt to provide an appliance that is capable of mixing the techniques utilizes a standard edgewise bracket having a bandside occlusogingivally extending slot for receiving a light wire insert pin. The tail of the pin is bent over the bracket to secure it in place and the head of the pin includes a round archwire slot vertically displaced from the rectangular arch wire slot and which is open labiobuccally but may be closed following the disposition of an archwire in the slot. This appliance can therefore be converted for use in the edgewise system to use in the light wire system by utilization of the light wire insert pin. This appliance is not acceptable because the light wire slot is at a substantially different level from the rectangular wire slot.

It has also been known to provide an appliance that may be converted from a light wire appliance to a rectangular appliance, as shown in U.S. Pat. No. 4,212,638. This appliance in its initial form is a light wire bracket suitable for use in the light wire technique and to have a round wire secured to it by a suitable lock pin. Alternative to securing a round archwire to the light wire bracket, an edgewise insert is provided which may be locked to the light wire bracket to convert it into an edgewise appliance. This appliance is likewise objectionable in that the archwire for the light wire technique is at a substantially different level on the appliance than an edgewise wire used in the edgewise technique. Moreover, the addition of the edgewise attachment for converting the appliance to an edgewise appliance elongates the appliance, thereby making it bulky for the mouth. By virtue of the different levels for the archwire, it becomes necessary to place this appliance near the gingival and away from the incisal edge to avoid subjecting it to occlusion forces.

SUMMARY OF THE INVENTION

The combination light wire and edgewise wire appliance of the present invention includes a conventional light wire bracket and a unique edgewise module. While the light wire bracket may be one of many forms, the model TP 256 bracket made by TP Laboratories, Inc. is a satisfactory version and is illustrated in the drawings for purposes of disclosing the present invention. Such a light wire bracket includes a body of U-shape having attaching flanges at the open end which is usually the lingual, wherein the U-shaped body defines an occlusogingivally extending lock pin opening or channel. A mesiodistally extending archwire slot is formed on the body at the gingivolingual corner and in coaction with the attaching flanges.

The edgewise module may be one of several various forms which mates with the body of the light wire bracket and which includes a mesiodistally extending rectangular archwire slot disposed at substantially the same level as the archwire slot for the light wire bracket. The usual ligating wings are provided on the edgewise module for facilitating the ligating of rectangular archwire in the archwire slot.

In operation, the light wire bracket is suitably attached to a tooth band or a direct bonding base, either of which would in turn be attached to a tooth. The light wire bracket is intended to have associated with it the usual round archwire which is connected thereto in the usual manner by a suitable lock pin. Conversion to use with the edgewise system merely involves removal of any lock pin or archwire and the mounting of the edgewise module onto the light wire bracket. Thereafter, the usual rectangular archwire can be ligated to the edgewise module which effectively attaches the wire to the tooth on which the light wire bracket and the edgewise module is disposed.

One form of edgewise module includes a ring-shaped base that fits over the body of the light wire bracket and against the attaching flanges. A retaining pin is then disposed in the module and coacts with the light wire bracket body for securing the module to the bracket. Another version includes a ring-shaped base on the edgewise module which can be deformed once in position on the bracket to lock the module to the bracket. A still further form of module differs in that the base is formed so that the module can be slid onto the bracket and which has legs coacting with the bracket body, at least one of which can be bent over the bracket body to secure the module to the bracket. Still another form of module includes locking and positioning detents or tabs which coact with the vertical archwire slot of the Begg bracket to define a snap-fit relationship between the module and the bracket.

It will be appreciated that with respect to any of the edgewise module versions, the rectangular archwire slot of the module would be disposed at substantially the same level as the archwire slot of the light wire bracket when the module is mounted on the bracket, thereby facilitating the initial positioning of the light wire bracket on the tooth. Moreover, the overall height of the appliance, whether used in the light wire or the edgewise mode, is about the same.

It is therefore an object of the present invention to provide a new and improved orthodontic appliance for selective use in the light wire or the edgewise technique and which may be easily converted for use with either technique and which places the archwire slots for each technique at about the same level.

A further object of the present invention is to provide a combination light wire and edgewise appliance that may be selectively used in either the light wire or the edgewise system and which includes a conventional light wire bracket and an edgewise module that may be easily mounted on the bracket and which will enable the disposition of the rectangular archwire used with the module to be at the same level as would be the round wire usable with the light wire bracket but at various angular positions.

Other objects, features and advantages of the invention will be apparent from the following detailed disclosure, taken in conjunction with the accompanying sheets of drawings, wherein like reference numerals refer to like parts.

BRIEF DESCRIPTION OF THE DRAWINGS

FIG. 1 is an exploded perspective view of one form of the appliance of the present invention;

FIG. 2 is a perspective view of the light wire bracket of the appliance of FIG. 1 as utilized to mount a round archwire to a tooth where treatment by the light wire technique is desired;

FIG. 3 is a perspective view of the appliance of the invention showing the edgewise module mounted on the light wire bracket and secured in place by the retaining pin and also showing attached to the module a rectangular archwire for use with the appliance in the edgewise technique and illustrating a rectangular archwire ligated to the edgewise module;

FIG. 4 is a front elevational view of the edgewise module shown in FIG. 1;

FIG. 5 is a side elevational view of the edgewise module of FIG. 1;

FIG. 6 is a rear elevational view of the edgewise module of FIG. 1;

FIG. 7 is a top plan view of the edgewise module of FIG. 1;

FIG. 8 is a bottom plan view of the edgewise module of FIG. 1;

FIG. 9 is a vertical sectional view taken through the appliance substantially along line 9—9 of FIG. 3;

FIG. 10 is a vertical sectional view taken substantially along line 10—10 of FIG. 9;

FIG. 11 is a vertical sectional view taken substantially along line 11—11 of FIG. 9;

FIG. 12 is a perspective view like FIG. 3 but illustrating a modified edgewise module according to the invention and illustrating a rectangular archwire ligated to the edgewise module;

FIG. 13 is an exploded perspective view of the embodiment of FIG. 12;

FIG. 14 is a perspective view like FIG. 12 but illustrating a still further modification of the edgewise module according to the invention and illustrating a rectangular archwire ligated to the edgewise module;

FIG. 15 is an exploded view of the appliance shown in FIG. 14 with the archwire and ligature omitted;

FIG. 16 is a front elevational view of the edgewise module shown in FIGS. 14 and 15 and illustrating in phantom lines the manner in which the ring-shaped base may be deformed for locking to the light wire bracket;

FIG. 17 is a perspective view like FIG. 12 of the appliance according to the invention and which includes a still further modified edgewise module with a rectangular archwire ligated thereto;

FIG. 18 is a top plan view of the appliance as shown in FIG. 17 with the retaining pin omitted for purposes of clarity;

FIG. 19 is a perspective view of the appliance according to the invention but illustrating a still further modified edgewise module and to which is ligated a rectangular archwire;

FIG. 20 is an exploded perspective view of the appliance shown in FIG. 19;

FIG. 21 is a vertical sectional view taken through the appliance of FIG. 19 and substantially along line 21—21;

FIG. 22 is a perspective view of an appliance according to the invention like FIG. 19 but which includes a still further modified edgewise module and to which is ligated a rectangular archwire;

FIG. 23 is an exploded perspective view of the appliance of FIG. 22;

FIG. 24 is a vertical sectional view taken through the appliance of FIG. 22 substantially along line 24—24;

FIG. 25 is a vertical sectional view taken through a modified edgewise module mounted on a Begg bracket which differs from the embodiment of FIG. 24 in that the pin opening is clear for the purpose of mounting other auxiliaries;

FIG. 26 is a perspective view of the edgewise module shown in FIG. 25;

DESCRIPTION OF THE PREFERRED EMBODIMENTS

Figure 27:
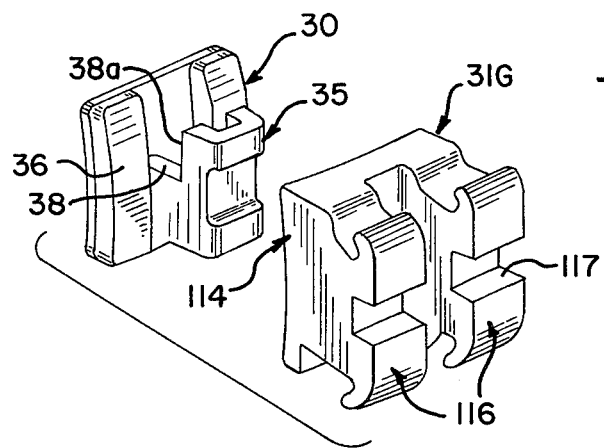
FIG. 27 is an exploded perspective view of still another embodiment of the invention.

Referring now to the drawings, the combination light wire and edgewise appliance of the present invention includes generally a conventional light wire bracket and an edgewise module. While several versions of the edgewise module are illustrated and will be described hereafter, the same light wire bracket is illustrated with each of the module versions. The appliance is useful in the light wire technique by mounting a round wire directly to the light wire bracket, and it may be used in the edgewise technique by mounting the edgewise module onto the light wire bracket and thereafter mounting a rectangular archwire to the edgewise module.

It should also be appreciated that the appliance of the invention may be mounted on the labiobuccal surface of the tooth when it is desired to likewise lock the archwire on that side of the tooth or the appliance may be mounted on a lingual surface of a tooth when it is desired to mount the archwire lingually of the teeth. For purposes of further describing the appliance of the invention, the terminology employed will consider mounting of the archwire labiobuccally of the teeth.

The appliance of the invention utilizing one version of the edgewise module, as shown in FIGS. 1 to 11, includes generally a conventional light wire bracket 30, an edgewise module 31, and a retention pin 32. Use of the appliance in the light wire mode is illustrated in FIG. 2 and in the edgewise mode in FIG. 3.

The light wire bracket 30 includes a U-shape in cross section body 35 having attaching flanges 36 at the lingual side of the bracket. The U-shaped body defines an occlusogingivally extending lock pin opening or channel 37. The gingivolingual corner of the body is notched to define in coaction with the attaching flanges 36 a vertically opening mesiodistally extending archwire slot 38. A space between the flanges is disposed lingual of the archwire slot. Thus, the bracket includes vertically adjacent each other from front to back, the pin opening, the archwire slot, and the space between the flanges. The light wire bracket 30 is shown in mounted relation on a standard direct bonding mesh base 39 which in turn would be direct bonded to a tooth surface by use of any suitable direct bonding adhesive. It should also be appreciated that the attaching flanges may be either soldered or spot-welded to the base and also that the bracket may be likewise mounted on a tooth band which in turn would be suitably cemented to a tooth.

The edgewise module 31 may be suitably cast and/or milled from a suitable material and includes a base portion 42 of somewhat ring shape and an edgewise bracket portion 43 on the labiobuccal side of the base. The bracket portion 43 includes a conventional horizontally opening rectangular archwire slot 44 and ligating wings or tie wings 45. The ring-shaped base 42 includes a central opening 46 sized to receive the body 35 of the light wire bracket when the module is mounted on the bracket. The bracket portion 43 is in the form of twin bars extending from the base such that a portion of each bar will be disposed on opposite sides of the light wire bracket body when the module is mounted on the bracket. As viewed in FIG. 4, the twin bars are connected at the top by a cross bar 48 and at the bottom by a cross bar 49. A short lug 50 extends downwardly from the upper cross bar 48 which necessitates tilting of the module during placement onto the light wire bracket with the upper end being tilted inwardly such that the lug 50 is disposed within the lock pin channel and the lower end then being swung downwardly onto the bracket body. Lug 50 coacts with the lock pin channel 37 to assist in preventing rotation of the module on the bracket. The lingual surface 51 of the module base is formed to mate with the labiobuccal surfaces of the attaching flanges 36 so that the module fits snugly with the flanges as particularly illustrated in FIGS. 3 and 9. Shoulders 52 are provided to engage the upper edges of the bracket body 35 to position the module occlusogingivally of the bracket.

The module is secured to the bracket by the retaining pin 32 which is inverted U-shape and includes a front or labiobuccal leg 54 and a back or lingual leg 55 extending downwardly from the pinhead 56. The front leg 54 is dimensioned to fit snugly in the lock pin channel 37 of the light wire bracket and is of such a length that when the pin is fully inserted the lower or tail end of the leg 54 may be bent over the edgewise module, as shown in FIGS. 9 and 10, to lock the pin in place and the edgewise module onto the light wire bracket. The upper end 55a of the rear leg 55 is of such a width as to snugly fit between the attaching flanges 36 of the light wire bracket, as illustrated in FIG. 11, while the lower end 55b of the leg is narrower in width to fit in the body of the bracket, as also seen in FIG. 11. Moreover, the length of the rear leg 55 is such that it goes to or extends just beyond the lower or occlusal end of the edgewise module, as illustrated in FIGS. 9 and 11. In order for the edgewise module 31 to accommodate the retaining pin 32, the upper cross bar 48 is provided with an open slot 60, while the lower cross bar 49 is provided with a pin hole 61. The front leg 54 matingly engages in the slot 60 and extends through the pin hole 61 before the tail of the leg is then bent over the edgewise module, as seen in FIG. 10.

The appliance of the invention including the light wire bracket, the edgewise module and the pin may be made of any suitable material such as metal or plastic. Preferably, the appliance will be made of metal, and it will be appreciated that the retention pin 32 will be made such that the tail of the front leg is easily bendable to secure the pin in place, as above mentioned. Likewise, the base 39 preferably would be made of the same material as the light wire bracket.

In operation, when the combination light wire and edgewise appliance of the invention is used in the light wire mode, the light wire bracket 36 will be used exclusive of the edgewise module, as illustrated in FIG. 2, and wherein a round archwire 64 will be disposed in the archwire slot 38 and locked in place by a conventional lock pin 65 in the usual manner.

When it is thereafter desired to use the appliance in the edgewise mode, the lock pin and round archwire would be removed so that the edgewise module 31 can be mounted in place on the light wire bracket and secured in place by means of the retention pin 32. At that point, as shown in FIG. 3, a rectangular archwire 68 would be matingly disposed in the rectangular archwire slot 44 of the module and ligated to the module by means of a ligature 69. The ligature 69 as illustrated is elastic, but it should be appreciated that wire ligatures could be used if so desired. Moreover, while the archwire appears to be square in cross section, it may be rectangularly shaped as a ribbon archwire if desired. In order to reduce the overall labiolingual depth of the appliance, a mesiodistally extending slot 72 is formed in the labiobuccal side of body 35 for clearance with the lingual side of the rectangular archwire 68, as particularly illustrated in FIG. 9. It may also be seen in FIG. 9 by looking at the depth of the light wire bracket archwire slot and the position of the edgewise module archwire slot that the rectangular archwire is disposable on the appliance at substantially the same level as the round archwire used in the light wire mode. It is further significant that the rectangular archwire is essentially positioned centrally between the gingival and occlusal ends of the appliance. These features facilitate the ease of placement of the appliance on the teeth and eliminate the chance of damage to the appliance during mastication. The slot 72 is sized vertically to allow vertical and angular displacement of the archwire slot in the edgewise module as desired in the straight wire technique, and horizontally such that the edgewise wire can be angularly disposed without engaging the light wire bracket.

Following use of the appliance in the edgewise mode should it be desirable to thereafter use the appliance in the light wire mode, it is only necessary to remove the rectangular archwire, the retaining pin 32 and the edgewise module so that the archwire slot of the light wire bracket is exposed for receiving a round archwire which can then be secured in place by a lock pin.

A modified appliance according to the invention is illustrated in FIGS. 12 and 13 which differs from the embodiment of FIGS. 1 to 11 only in that the edgewise module is segmentally fabricated. The retention pin is also slightly modified.

In this embodiment the edgewise module, generally designated by the numeral 31A, includes a ring-shaped base 76 that may be stamped of suitable metal and have attached thereto a pair of edgewise bars 77. The bars 77 may be suitably soldered or spot-welded to the ring-shaped base 76. The opening 78 through the base 76 is formed such that the module may be applied directly onto the light wire bracket lingually without tilting of the module. An indent 79 at the top of the base 76 defines on opposite sides a pair of shoulders 80 which engage the upper edges of the bracket body and prevent the base from falling into the archwire slot. Thereafter, the retention pin 32a is applied for locking the module to the bracket. The pin 32a differs from the pin 32 in the first embodiment only in that the head is of a slightly different configuration, although it can be appreciated that these retention pins may be interchangeably used. The operation of the appliance of FIGS. 12 and 13 would be the same as the embodiment of FIGS. 1 to 11.

Another embodiment is illustrated in FIGS. 14 to 16 which differs from both previous embodiments in that it does not use a retention pin, and from the embodiment of FIGS. 12 and 13 in that the base is deformable for purposes of locking the edgewise module to the light wire bracket. The edgewise module in this embodiment is generally designated as 31B, and it includes a ring-shaped base 82 having twin edgewise bars 83 suitably secured thereto such as by soldering or spot-welding. Extending from the upper and lower portions of the base 82 are upper and lower locking lugs 84 and 85 sized so that when the ring is squeezed or deformed to the position shown to phantom in FIG. 16, they will move into the lock pin channel of the light wire bracket and lock the module to the body of the light wire bracket. Shoulders 86 engage the upper edges of the bracket body. Thus, when it is desired to use the appliance of this embodiment in the edgewise mode, the edgewise module 31B is mounted onto the light wire bracket so that a rectangular archwire can be secured to the module.

Referring now to FIGS. 17 and 18, a modified appliance of the invention is illustrated which differs from the other embodiments and particularly from the embodiment of FIGS. 12 and 13 in that the edgewise module 31C is wider so as to more completely cover the light wire bracket. Since the module is wider than the mesiodistal width of the light wire bracket, the base upon which the light wire bracket is mounted is enlarged over that shown in the previous embodiments. This modified edgewise module includes a base 88 to which twin edgewise bars 89 are suitably attached as in the embodiments of FIGS. 12 and 13 and 14 to 16. Because the base is wider, the twin bars are also disposed further apart, as particularly seen in FIG. 18. The wider frame 88 has inwardly turned portions 90 at the mesial and distal sides to wrap over the edges of the light wire bracket attaching flanges and engage the mesh base 39 which provides better stability between the edgewise module and the light wire bracket and enhances rotational resistance. While a retention pin like that shown in FIG. 12 is illustrated for attaching the edgewise module 31C to the light wire bracket, it may be appreciated that the base 88 may also be made squeezable or deformable like the embodiment of FIGS. 14 to 16 which would eliminate the need for a retention pin.

Another modified edgewise module is shown in FIGS. 19 to 21, where the module is generally designated as 31D. This module differentiates from those of the previous embodiments primarily in that it is mountable on the light wire bracket 30 by sliding it onto the bracket body from the occlusal or gingival. The module includes a base 94 having a pair of downwardly extending outer legs 95 which become disposed at opposite sides of the bracket body 35 when the module is mounted onto the bracket and a central leg 96 which is in the form of a pin that enters into the lock pin channel 37 of the bracket. The length of the central leg 96 is such that the lower end 97 defines a tail which extends beyond the bracket when the module is first positioned on the bracket so that it can be bent over as shown at 97a in FIGS. 19 and 21 to firmly secure the module to the bracket. Twin edgewise bars 98 are suitably secured to the base 94. Shoulders 99 are provided on opposite sides of the central leg 96 to limit the downward movement and coact with the bottom of the bracket archwire slot to centrally position the edgewise bars relative to the bracket.

When the module is in position on the bracket and locked thereto, the rectangular archwire 68 may then be disposed in the rectangular archwire slot of the module 31D and ligated thereto by a ligature 69 in the usual fashion. As also seen in FIGS. 19 and 21, the lingual surface of the base 94 is formed in the areas of the light wire bracket attaching flanges 36 to snugly bear against the flanges. Thus, the outer legs 95 align with the flanges 36. Moreover, the labiolingual dimension of the central leg 96 is such as to fill the forward part of the lock pin channel, as seen particularly in FIGS. 19 and 21, so that a snug fit will be established between the bracket and the module and to prevent any labial or lingual movement of the module on the bracket. Thus, the module has a self-contained locking feature for locking it onto the light wire bracket. When removing the module from the bracket, it is only necessary to either straighten the tail 97 to its original position, as shown in FIG. 20, or clip the bent-over end with a cutter.

It may be further appreciated that the base of this module differs from the bases of the previous modules in that it is not ring-shaped and that the only part of the module which resists movement on the bracket upwardly as in the drawings is the bent-over tail 97. While the central leg 96 may be formed integrally with the base 94 after which the twin edgewise bars 98 may be suitably secured to the base, it may also be appreciated that the base may be made as a U-shaped piece and the central leg 96 thereafter suitably secured to the base. Further, the occlusogingival depth of the central part of the base is such that it will extend into the light wire bracket archwire slot and sit on the bottom of a slot, as shown in FIG. 21, and the central leg 96 is attached to that area and functions as the retention pin for the module.

A similar but slightly different slide-on edgewise module is shown in FIGS. 22 to 24 and generally designated as 31E. This module differentiates from that in FIGS. 19 to 21 in the provision of additional stabilizing means for inhibiting rotational and mesiodistal movement of the module relative to the bracket.

The edgewise module 31E includes a base 102 having outer legs 103 and a central leg 104. Twin edgewise bars 105 are suitably secured to the outer legs 103 of the base. A lingually extending stabilizing bar or projection 106 fits between the opposed attaching flanges 36 of the light wire bracket 30, as seen particularly in FIG. 22 and also in FIG. 24 to coact with the flanges and prevent rotational and mesiodistal movement between the module and the bracket. The occlusogingival length of the bar or projection may be equal to or less than the depth of the bracket archwire slot. The stabilizing bar or projection is in general vertical alignment with the mesial and distal walls of the bracket body.

The central leg 104 may be initially formed integrally with the base or separately formed and thereafter suitably secured to the base. As seen particularly in FIG. 23, shoulders 107 are provided on opposite sides of the leg which bottom in the bracket archwire slot and dispose the edgewise bars centrally of the bracket before the tail 108 is bent over one of the bracket attaching flanges. After the tail 108 is bent laterally against one of the attaching flanges as shown at 108a in FIG. 22 at a position close to the tooth, the most possible room for ligating the rectangular archwire to the edgewise module is provided. Like the embodiment of FIGS. 19 to 21, mounting of the edgewise module 31E to the light wire bracket merely requires it to be slid onto the bracket to bottom in the slot and to thereafter bend the tail to lock the module in place. Similarly, the module may be removed in the same fashion as above described for removal of the module 31D from the bracket.

Another form of slide-on edgewise module is illustrated in FIGS. 25 and 26 and generally indicated by the numeral 31F. The module generally includes a T-shaped frame or base 109 having formed thereon or attached thereto in a suitable manner a pair of edgewise bars 110. This version differs primarily from the embodiment of FIGS. 22 to 24 in that it leaves the pin opening 37 clear, as seen particularly in FIG. 25, so that auxiliaries such as a rotating spring or an uprighting spring may be mounted on the appliance to coact with the archwire. Particularly, the tail of such a spring would be received within the pin opening.

The T-shaped frame 109, as seen most clearly in FIG. 26, includes a generally U-shaped head 112 in inverted position and a lingually offset tail 113. The head and tail are received in and along the archwire slot of the Begg bracket 30 although the tail generally extends into the space between the welding flanges. The tail 113 is bent over a flange of the Begg bracket to secure the module to the bracket. The front face of the head 112 engages the vertical edges of the archwire slot while the rear face would engage the welding flanges 36 to prevent labiolingual movement. The downwardly extending ears 109a of the frame are disposed on opposite sides of the body to engage the mesial and distal sides of the body and prevent mesiodistal movement of the module relative to the bracket. Shoulders 109b of the frame bottom on the horizontal edges of the bracket archwire slot. Otherwise, the edgewise module functions the same as the previously described modules in that it provides a pair of edgewise bars for mounting the rectangular wire at substantially the same level as the Begg bracket mounts the round wire to convert the appliance for use in edgewise treatment.

Figure 28:
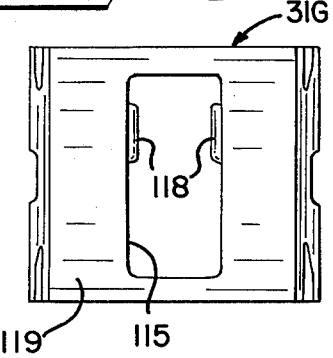
FIG. 28 is a rear elevational view of the edgewise module of FIG. 27.
Figure 29:
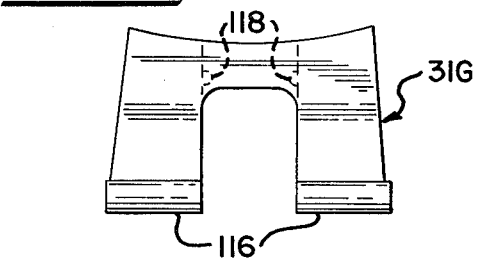
FIG. 29 is a top plan view of the edgewise module of FIG. 27.
Figure 30:
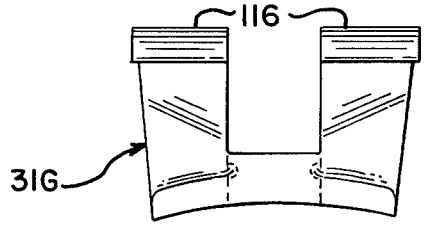
FIG. 30 is a bottom plan view of the edgewise module of FIG. 27.
Figure 31:
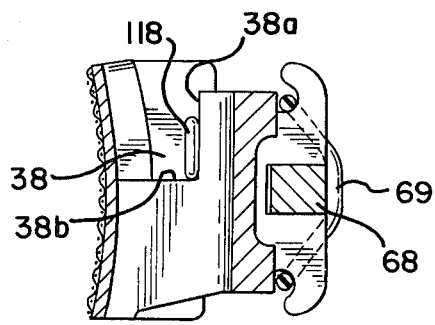
FIG. 31 is a vertical sectional view taken through the center of the edgewise module of FIG. 27 as mounted on a light wire bracket to illustrate the coaction between one of the detents and the vertical slot of the light wire bracket and also illustrating an edgewise wire ligated to the edgewise module.

Another form of edgewise module is shown in FIGS. 27 to 31 and generally designated as 31G, which may be snap-locked into place on the light wire bracket 30.

Edgewise module 31G includes a base 114 which is ring-shaped in that it includes an opening 115 for receiving the body 35 of the light wire bracket 30. Projecting forwardly from the base 114 are the ligating wings or tie wings 116 in which are formed the horizontally opening edgewise archwire slot 117. The size of the opening 115 in the module is such that it will allow the module to slide over the body of the light wire bracket, and for locking the module in place a pair of locking detents or tabs 118 are disposed at the module opening 115 and extend inwardly for locking to the vertically opening archwire slot 38 of the light wire bracket 30.

The tabs 118 are positioned at a level such that when the module is snap-fit into position on the light wire bracket, the rear face 119 of the module will be in abutting engagement with the welding flanges 36 of the light wire bracket and the tabs will snap into place behind the vertical edge 38a of the vertically opening archwire slot 38. Further, the lower ends of the locking tabs 118 will engage the horizontal edge 38b of the archwire slot so as to further orient the module on the bracket and prevent it from moving downwardly. Because the base 114 of the module is of heavier construction than the body of the light wire bracket, the light wire bracket body will flex upon urging the module onto the bracket to allow the tabs to move over the side walls of the body and into locking position with respect to the archwire slot 38 of the bracket. It therefore can be appreciated that with this embodiment it is not necessary to use a retaining pin to retain the module in position on the light wire bracket or to provide a bendable tail. The module will be mounted into snap-locked position by lining up the module opening with the bracket and the locking tabs with the vertical slot and then pressing the module onto the bracket.

The ring-shaped base may also be split at one end to allow the sides to be squeezed together. To facilitate squeezability the module may be made of dead soft material, although it would even be possible to otherwise squeeze an appliance made of the standard material. In any event, the integrity of the archwire slot on the module would not be adversely affected.

In order to provide additional anti-rotation between the edgewise module and the light wire bracket, the module may include lingually extending stops or tabs to coact with the gingival or occlusal ends of the attaching flanges. Such stops or tabs would fit over or hook over the ends of the attaching flanges and generally extend mesiodistally. With respect to the ring versions of FIGS. 1 to 18 and 27 to 31, the stops may be at either or both the gingival and occlusal ends of the module, while they would be disposed at the ends opposite the tails in the versions of FIGS. 19 to 26.

It will be appreciated that the rectangular archwire slot shown in each of the edgewise modules is of the conventional form and that it may take other forms for making the module in the "straight wire" technique. Thus, the archwire slot may have various angulations and torques built into the module as well as various labio lingual depths. Further, various depths can be provided by adjusting the thickness of the base. Accordingly, whatever version of the module is used, it may have various forms for the orthodontist to choose from so that the straight wire technique may be performed.

From the foregoing, it can be appreciated that the appliance of the invention is especially useful to the orthodontist to interchangeably employ both the light wire and edgewise systems during the treatment of a patient without necessitating the remounting of brackets on the teeth as the same light wire bracket can be used throughout treatment either to be used in the light wire technique or as a mounting for an edgewise module. Significantly, the vertical levels of the archwire slots are about the same.

It will be understood that modifications and variations may be effected without departing from the scope of the novel concepts of the present invention, but it is understood that this application is to be limited only by the scope of the appended claims.

The invention is hereby claimed as follows:

1. An orthodontic appliance for use in the light wire or the edgewise system comprising, a light wire bracket attachable to a tooth, said bracket having a mesiodistally extending and vertically opening archwire slot and an occlusogingivally extending lock pin channel, and an edgewise module mountable on said bracket, said module having a mesiodistally extending and labiobuccally opening rectangular archwire slot disposed at substantially the same vertical level as said archwire slot in said bracket.

2. The orthodontic appliance defined in claim 1, wherein said module includes a base formed to mate with said bracket and be secured thereto.

3. The orthodontic appliance defined in claim 2, which further includes means for locking said module to said bracket.

4. The orthodontic appliance defined in claim 3, wherein said locking means includes a retaining pin coacting with the module base and bracket to secure the module to the bracket.

5. The orthodontic appliance defined in claim 3, wherein the module base is ring-shaped, and said locking means is integral with the module with the module base being deformable to coact with the bracket archwire slot and be secured to the bracket.

6. The orthodontic appliance defined in claim 3, wherein the module base includes means slidable into said lock pin channel and said archwire slot of said bracket.

7. The orthodontic appliance defined in claim 6, wherein said locking means includes a tail integral with the module and bendable over the bracket to secure the module thereto.

8. The orthodontic appliance defined in claim 3, wherein said locking means includes detent means coacting with the bracket to snap-lock the module onto the bracket.

9. The orthodontic appliance defined in claim 8, wherein said detent means coacts with said vertical archwire slot of said bracket.

10. The orthodontic appliance defined in claim 9, wherein said detent means includes a pair of opposed detents on said module base.

11. A combination light wire and edgewise appliance comprising a light wire bracket and an edgewise module, said bracket having a U-shape in cross section body defining an occlusogingivally extending pin opening, attaching flanges at the lingual side of the body adapted to be attached to a bracket base or a band, and a vertically opening-mesiodistally extending archwire slot defined by the attaching flanges and a notch in the body, whereby said bracket is adapted to receive a round archwire in said slot and a lock pin in said pin opening for retaining the archwire to the bracket for light wire system use, said module having a base for coacting with said bracket body to be retained thereby, a pair of spaced edgewise bars extending from the module base and including a horizontally opening-mesiodistally extending rectangular archwire slot disposed at substantially the same level as said bracket archwire slot when the module is mounted on the bracket, and ligating wings, whereby mounting said module on said bracket permits edgewise system use including the mounting of rectangular wire in the archwire slot and ligating the wire to the ligating wings.

12. The appliance defined in claim 11, wherein the module base and edgewise bars are integrally formed in one piece.

13. The appliance defined in claim 11, wherein the module base and edgewise bars are separately formed and assembled by attaching the bars to the base.

14. The appliance defined in claim 11, wherein said base of said edgewise module is ring-shaped to encircle the bracket body when mounted on the bracket.

15. The appliance defined in claim 14, which further includes a retention pin engageable with said bracket and said module to secure the module to the bracket.

16. The appliance defined in claim 15, wherein the retention pin includes a head and front and back legs extending therefrom, said pin straddling the module base with the back leg being received between the attaching flanges and the front leg extending through said pin opening and being bendable over the bottom of the bracket to lock the module onto the bracket.

17. The appliance defined in claim 14, wherein said module base is deformable and provided with upper and lower legs movable into the pin opening of the bracket upon being deformed to lock the module onto the bracket.

18. The appliance defined in claim 11, wherein the module base is formed to be slidably mounted on the bracket.

19. The appliance defined in claim 11, wherein the module base includes at the mesial and distal sides lingually extending stabilizing means coacting with the mesial and distal edges of the bracket attaching flanges and/or the bracket base or band.

20. The appliance defined in claim 11, wherein the module base includes a pair of parallel outer legs and a central leg extending from a head, the outer legs fitting along the mesial and distal sides of the bracket body and the central leg extending through the pin opening, and the central leg being of such a length as to extend beyond the bracket body and define a tail to be bendable against the body to lock the module onto the bracket.

21. The appliance defined in claim 20, wherein the module base includes lingually extending stabilizing means coacting with the bracket attaching flanges and/or the bracket base or band.

22. The appliance as defined in claim 20, wherein the tail is bendable over one of the attaching flanges.

23. The appliance as defined in claim 14, wherein said module base further includes means for snap-locking said module onto said bracket.

24. The appliance as defined in claim 23, wherein said snap-locking means includes detent means coacting with the vertically opening archwire slot of said bracket.

25. The appliance as defined in claim 24, wherein said detent means includes a pair of opposed detents on said module base.

26. The appliance defined in claim 11, wherein said bracket further includes a mesiodistally extending notch in the labial face of said bracket body in alignment with the archwire slot of said module.

27. The appliance defined in claim 26, wherein said notch is vertically and horizontally sized to freely allow an archwire on said module to be disposed closer to said tooth and to be angularly oriented to said bracket.

28. The appliance defined in claim 11, wherein said module base is received by said bracket archwire slot thereby leaving the pin opening clear for mounting of auxiliaries, and said module base includes ears extending along opposite sides of said bracket body and a lingually offset tail bendable over an attaching flange.

* * * * *